United States Patent [19]

Tomotake et al.

[11] Patent Number: 5,100,773

[45] Date of Patent: Mar. 31, 1992

[54] SILVER HALIDE COLOR PHOTOGRAPHIC LIGHT-SENSITIVE MATERIAL CONTAINING AMIDE TYPE COUPLERS

[75] Inventors: Atsushi Tomotake; Shuji Kida; Mayumi Tomotake; Fumio Ishii, all of Hino, Japan

[73] Assignee: Konica Corporation, Tokyo, Japan

[21] Appl. No.: 441,313

[22] Filed: Nov. 27, 1989

[30] Foreign Application Priority Data

Nov. 29, 1988 [JP] Japan .................................. 63-302626
Nov. 29, 1988 [JP] Japan .................................. 63-302627

[51] Int. Cl.⁵ .............................................. G03C 7/36
[52] U.S. Cl. ........................................ 430/557; 430/389
[58] Field of Search ............................... 430/557, 389

[56] References Cited

U.S. PATENT DOCUMENTS

| | | | |
|---|---|---|---|
| 4,401,752 | 8/1983 | Lau ........................................ | 430/557 |
| 4,824,773 | 6/1988 | Sato et al. ........................... | 430/557 |
| 4,842,994 | 6/1989 | Sakanoue et al. .................. | 430/957 |
| 4,977,073 | 12/1990 | Ishige et al. ......................... | 430/547 |

FOREIGN PATENT DOCUMENTS

| | | | |
|---|---|---|---|
| 322904 | 7/1989 | European Pat. Off. . | |
| 2237448 | 10/1987 | Japan .................................. | 430/557 |
| 3133151 | 6/1988 | Japan .................................. | 430/557 |
| 1231049 | 9/1989 | Japan .................................. | 430/557 |

OTHER PUBLICATIONS

Patent Abstracts of Japan, vol. 12, No. 125 (p.61) [2972]; 4/19/88.
JPA-62-250446: 10/31/87.

Primary Examiner—Charles L. Bowers, Jr.
Assistant Examiner—Lee C. Wright
Attorney, Agent, or Firm—Jordan B. Bierman

[57] ABSTRACT

There is disclosed the silver halide light-sensitive color photographic material having an excellent dispersing stability in a silver halide emulsion, a satisfactory color formability and a sufficient maximum color density, and capable of providing a high reactivity or a high quality image, wherein the photographic material contains at least one selected from the couplers represented by Formulas I and II:

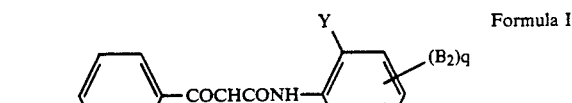

Formula I

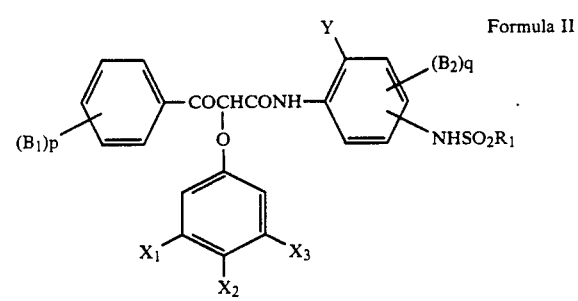

Formula II

2 Claims, No Drawings

SILVER HALIDE COLOR PHOTOGRAPHIC LIGHT-SENSITIVE MATERIAL CONTAINING AMIDE TYPE COUPLERS

FIELD OF THE INVENTION

The present invention relates to a silver halide color photographic light-sensitive material containing an active-site-substituted-type yellow dye forming coupler having an excellent color formability.

BACKGROUND OF THE INVENTION

In a color photograph, as is well known, couplers react with the oxidation product of an aromatic primary amine color developing agent, which is formed by developing a silver halide color photographic light-sensitive material, to thereby form a color image composed of dyes such as indophenol, indoaniline, azomethine, phenoxazone, quinoneimine, phenazine and dyes similar therto. A color reproduction is generally carried out by a subtractive color process, and there are used silver halide emulsions spectrally sensitive to blue, green and red, and couplers for forming yellow, magenta and cyan dyes, which are complementary colors for blue, green and red, respectively. There are generally used as a yellow dye forming coupler, the compounds having an active methylene group; as a magenta dye-forming coupler, a pyrazolone type, pyrazolobenzimidazole type, pyrazolotriazole type or indazolone type compounds; and as a cyan dye-forming coupler, a phenol type or naphthol type compounds.

Each of these couplers generally requires four silver atoms in order to form one molecule of a dye. Dut to the shortage of silver resources, silver-saving type couplers have been proposed; for example, the technique is disclosed in Japanese Patent Examined Publication No. 13576/1974 in which there is used a coupler having a splitting off group introduced to its active site for forming one molecule of a dye with two silver atoms, the so-called two equivalent coupler. This method enables to reduce by half the amount of silver required for a conventional four equivalent type coupler, so that two equivalent couplers have been widely used in recent years.

Though the known two equivalent couplers are effective to some extent, there are still demanded more improvements of the characteristics, particularly in the color formability. The coupler have been demanded to be more reactive to meet the recently prevailing requirements for higher sensitivity and higher image quality as well as saving of processing time. It is possible to increase the sensitivity of a light-sensitive material by raising the reactivity of a coupler to the oxidation product of a color developing agent. Further, more reactive coupler makes it possible to reduce the amounts of the coupler and silver halide without decreasing the sensitivity. As the result, the thickness of the light-sensitive material is reduced and the scattering of an incident light is decreased, resulting in improvement of the sharpness. In the negative and reversal light-sensitive materials, a blue-sensitive layer is provided nearest a light-incident side, so that reducing the thickness of the blue-sensitive layer is the most effective. Therefore, the development of especially high reactive yellow couplers has been expected.

On the other hand, in the developing process, benzyl alcohol is added to a conventional color developing solution to increase the color forming efficiency of a light-sensitive material. Benzyl alcohol is lable to cause an environmental pollution problem such as increase of a B.O.D. (biological oxygen demand) value. Accordingly, it is necessary to add less amount of benzyl alcohol in a color developing process. However, if the photographic material containing a conventional yellow coupler is developed in a processing solution containing less amount of bezyl alcohol especially in a shorter developing time, the density of a developed color image is lowered significantly. Thus, the development of a yellow coupler having a sufficient color formability even in developing with less amount of benzyl alcohol has also been expected. The conventional four-equivalent and two equivalent couplers cannot necessarily solve the above problems. On the contrary, two equivalent yellow couplers having a non-diffusible group and an aryloxy group as a splitting off group have been noted as ones capable of solving the above problems. The examples of the two-equivalent yellow couplers having a non-diffusible group include aryloxy-splitting off type two equivalent yellow couplers having a sulfamoyl or acylamino group disclosed in U.S. Pat. No. 3,644,498; ones having an alkoxycarbonyl group disclosed in Japanese Patent Publication Open to Public Inspection (hereinafter referred to as Japanese Patent O.P.I. Publication) No. 174839/1984; and an alkyl or arylsulfamoyl group disclosed in Japanese Patent O.P.I. Publication No. 69653/1985. These couplers are known to be significantly improved in a color forming efficiency particularly when there is introduced into a para-position of an aryloxy group thereof, an electron attractive group such as a sulfonyl group, a sulfamoyl group, a carbamoyl group, an acyl group, a formyl group, a nitro group and a cyano group. These couplers have a poor solubility in a high boiling solvent due to a non-diffusible group and a low dispersing stability in a silver halide emulsion. Obviously, this will cause a problem particularly when the amount of a high boiling solvent is reduced for a thinner layer which has been prevailing in recent years. Further, most of the couplers disclosed in the above patent publications are still not satisfactory in a coupling reactivity and a density of a formed color image, so that the coating amount thereof needs to be increased.

As the yellow coupler capable of meeting demands for improving both the solubility in a high boiling solvent and the high color formability, aryloxy-splitting off type two equivalent yellow couplers having a sulfonamido group as a nondiffusible group are described in U.S. Pat. No. 3,933,501. However, the couplers disclosed therein are pivaloylacetanilide yellow couplers having an inferior activity to benzoylacetanilide couplers, so that their color formability and solubility to solvents does not yet reach any satisfactory level. Japanese Patent O.P.I. Publication No. 43144/1988 describes yellow couplers having a sulfonamido group as a non-diffusible group, in which the solubility is improved by introducing a branched alkoxycarbonyl group into the para position to an oxygen atom of an aryloxy group. The couplers disclosed therein are pivaloylacetanilide couplers intended for improving an antifading property, and are unsatisfactory in color formability. Japanese Patent O.P.I. Publication No. 153955/1987 describes aryloxy-splitting off type two equivalent yellow couplers intended for improving both solubility and color formability by introducing a specific arylsulfonamido group. However, the arylsulfonamido group is inherently inferior in both solubility and dispersing stability in an emulsion, and the arylsulfonamido non-diffusible group of the couplers disclosed therein has a very complicated structure in order to improve the above matters. Thus, it is liable to increase the coupler's manufacturing processes, resulting in an increase in cost. Japanese Patent O.P.I. Publication No. 153954/1987 describes yellow couplers having a sulfonamido non-diffusible group and an aryloxy group having a cyano group in the para-position to the oxygen atom thereof. However, the majority of the couplers disclosed therein also are pivaloylacetanilide yellow couplers having an insufficient color formability level because of the above-mentioned reason.

Further, this publication also discloses benzoylacetanilide type aryloxy-splitting off two equivalent yellow couplers, however the aryloxy group in which a cyano group is merely introduced to the para-position is not enough to provide the sufficient activity and, therefore, these couplers have no sufficient color formability, either. The publication further discloses other yellow couplers having an aryloxy group with a cyano group introduced to the para-position and a chlorine atom to the ortho-position in order to raise the activity, however the color formability is still not sufficient. Moreover, the substituent introduced into the ortho-position results in reducing the coupler's solubility in a high boiling solvent.

U.S. Pat. No. 4,401,752, Japanese Patent O.P.I. Publication Nos. 228649/1984 and 250446/1987 describe that the color formability is further improved by introducing an electron attractive group, particularly a so-called polarizable group, to the ortho position of an aryloxy group. However, the couplers disclosed therein still have a poor solubility in a high boiling solvent and a low dispersion stability because of the above-mentioned reason.

On the other hand, it is proposed to improve a color formability by introducing a hydrophilic group into a non-diffusible group. For example, European Patent No. 0,073,636 describes that the color formability is improved by a non-diffusible group having on its terminal a hydroxyphenylsulfonyl group. However, the hydrophilic group introduced into the non-diffusible group reduces a dispersing stability of a coupler in an emulsion and further, the non-diffusible group becomes so complex as to result in increasing a manufacturing cost.

SUMMARY OF THE INVENTION

It is an object of the present invention to provide a high sensitive silver halide color photographic light-sensitive material comprising an inexpensive yellow coupler which has a sufficient dispersing stability in a silver halide emulsion, a satisfactory color formability and a sufficient maximum color density, and can provide a high reactivity or a high quality image.

The above object of the invention is accomplished by a silver halide color photographic light-sensitive material containing one selected from the couplers represented by the following Formulas I and II:

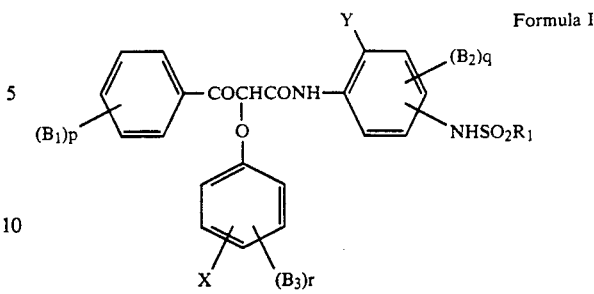

wherein $R_1$ represents a substituted or unsubstituted alkyl group; X represents a hydrophilic substituent; Y represents a halogen atom, an alkoxy group or an alkylamino group; $B_1$, $B_2$ and $B_3$ each represent a substituent; and p, q and r each represent an integer of zero to 3;

wherein $R_1$, Y, $B_1$, $B_2$, and p are synonymous with those defined in Formula I; $X_1$, $X_2$ and $X_3$ each represent a hydrogen atom and a substituent, provided that the sum of the Hammett's $\sigma m$ values of $X_1$ and $X_3$ and a Hammett's $\sigma p$ value of $X_2$ is not less than 0.67; and q represents an integer of 0 to 2.

DETAILED DESCRIPTION OF THE INVENTION

In Formulas I and II, the alkyl group represented by $R_1$ is a linear, branched or cyclic alkyl group having 1 to 30 carbon atoms, such as a t-butyl group, a n-hexyl group, a cyclohexyl group, a t-octyl group, a n-dodecyl group and a n-hexadecyl group. The alkyl group represented by $R_1$ may have a substituent such as an aryl group, a hydroxy group, an alkoxy group, an aryloxy group, a mercapto group, a thioalkyl group, a thioaryl group, an amino group, an alkylamino group, an anilino group, a carboxyl group, an alkoxycarbonyl group, an aryloxycarbonyl group, an alkylcarbonylamino group, an arylcarbonylamino group, a sulfamoyl group, an alkylsulfamoyl group, an arylsulfamoyl group, a sulfo group, an alkylsulfonyl group, an arylsulfonyl group, an alkylcarbonyl group, an arylcarbonyl group, a cyano group, a nitro group, a halogen atom, a carbamoyl group, an alkylcarbamoyl group, an arylcarbamoyl group, and a heterocyclic group.

In Formula I, X represents a hydrophilic substituent. The value for expressing a hydrophilic property is represented by a distribution coefficient log P widely used in the field of pharmacy, which represents the distribution of a solute in a water phase and a n-octanol phase in a dual-phase system of water and n-octanol; the smaller the value in a negative, the larger the hydrophilic property. The distribution coefficient value of each substituent and the calculation method thereof are detailed in R.

F. Rekker, 'The Hydrophobic Fragment Constant', Elsevier, New York, 1977. The hydrophilic property of the hydrophilic group in the invention is defined by that the log p of phenol corresponding to the aryloxy group having the hydrophilic group the corresponding phenol is 1 or less, and preferably zero or less.

The examples thereof include a sulfo group, an alkylsulfonyl group having 1 or 2 carbon atoms, a sulfamoyl group, an arkylsulfamoyl group having 1 to 5 carbon atoms, an amino group, an alkylsufonylamino group having 1 to 4 carbon atoms, an alkylcarbonylamino group having 1 to 3 carbon atoms, a perfluoroalkylcarbonylamino group having 1 to 6 carbon atoms, a carboxyl group, an alkoxycarbonyl group having 1 to 3 carbon atoms, a carbamoyl group, an alkylcarbamoyl group having 1 to 3 carbon atoms and a hydroxy group. Of these groups, the preferable ones are the alkylsulfonyl group, sulfamoyl group, alkylsulfamoyl group, alkylsulfonylamino group, perfluoroalkylcarbonylamino group, carbamoyl group and alkylcarbamoyl group. These substituents represented by X may further have substituents as long as the hydrophilic property thereof is not impaired, such as a hydroxy group, an amino group, a carboxy group, a carbamoyl group, a sulfo group, an alkyl group substituted with a sulfamoyl group, and the same substituent as defined for X.

The examples of the aryloxy group together with the log P values of the corresponding phenol compounds are shown below.

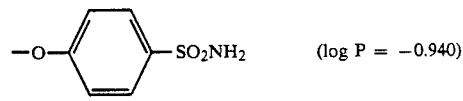 (log P = −0.940)

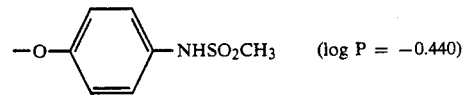 (log P = −0.440)

 (log P = −0.160)

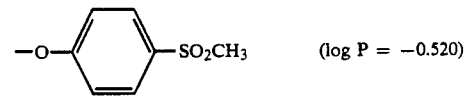 (log P = −0.520)

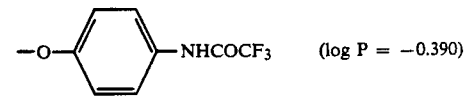 (log P = −0.390)

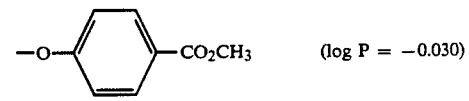 (log P = −0.030)

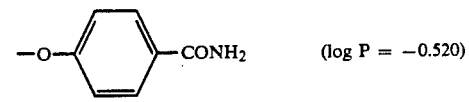 (log P = −0.520)

-continued

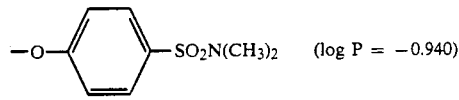 (log P = −0.940)

The group represented by Y in Formulas I and II includes a halogen atom, an alkoxy group and an alkylamino group, preferably a halogen atom and an alkoxy group, and most preferably a chlorine atom and a methoxy group.

In Formulas I and II, the substituent represented by $B_1$ includes a halogen atom, an alkoxy group, an aryloxy group, an acyloxy group, an alkylamino group, an anilino group and an acylamino group, p is an integer of zero to 3, provided that $B_1$'s may be the same when p is 2 or 3. In Formulas I and II, the substituent represented by $B_2$ includes a halogen atom, an alkoxy group, an aryloxy group, an acyloxy group, an alkylamino group, an anilino group and an acylamino group. q is an integer of zero to 3, provided that $B_2$'s may be the same when q is 2 or 3.

In Formula I, the substituent represented by $B_3$ includes a halogen atom, a nitro group, a cyano group, an alkoxy group, and the same substituents as defined for X. r is an integer of zero to 3, provided that $B_3$'s may be the same when r is 2 or 3.

Where the substituents represented by X and $B_3$ in Formula I comprise a polarizable group such as —CO— or —SO$_2$— like an alkylcarbonylamino group and an alkylsulfonyl group. X and $B_3$ preferably combine with an aryloxy group in the meta- or para-position to the oxygen atom thereof.

The coupler represented by Formula I may form a dimer, oligomer or polymer by combining with each other through a two or more valent group at any one of $R_1$, X, Y, $B_1$, $B_2$ and $B_3$, wherein the number of carbon atoms may deviate from the ranges defined for the respective groups.

In Formula II, the substituents represented by $X_1$, $X_2$ and $X_3$ make the sum of not less than 0.67 in the Hammett's $\sigma m$ values of $X_1$ and $X_3$ and the Hammett's $\sigma p$ value of $X_2$. Such substituents include a halogen atom, an alkyl group, an alkenyl group, an aryl group, a nitro group, an alkylsulfonyl group, an arylsulfonyl group, a cyano group, a carboxy group, an alkoxycarbonyl group, an aryloxycarbonyl group, a carbamoyl group, an alkylcarbamoyl group, an arylcarbamoyl group, an alkylcabonyl group, an arylcarbonyl group, a sulfo group, an alkylsulfonyl group, an alkylsulfamoyl group, an arylsulfamoyl group, an amino group, an alkylsulfonylamino group, an arylsulfonylamino group, an alkylcarbonylamino group, an arylcarbonylamino group, a hydroxy group, an alkoxy group, an aryloxy group, a mercapto group, a thioalkyl group, a thioaryl group, and a heterocyclic group; preferably, a hydrogen atom, a halogen atom, an alkenyl group, a nitro group, an alkylsulfonyl group, an arylsulfonyl group, a carboxy group, an alkoxycarbonyl group, an aryloxycarbonyl group, a carbamoyl group, an alkylcarbamoyl group, an arylcarbamoyl group, an alkylcarbonyl group, an arylcarbonyl group, an alkylsulfamoyl group, an arylsulfamoyl group, an alkylsulfonylamino group, an arylsulfonylamino group, an alkylcarbonylamino group, an arylcarbonylamino group, an alkoxy group, and an aryloxy group; and more preferably a hydrogen atom, a halogen atom, a nitro group, an alkylsulfonyl group, an arylsulfonyl group, and an alkoxy group. The combination of the substituents represented by $X_1$, $X_2$, and $X_3$ is arbitrary as long as the sum of the Hammett's $\sigma m$ values of $X_1$ and $X_3$ and the Hammett's $\sigma p$ value of $X_2$ is not less than 0.67. Moreover, the above substituents may have substituents as long as they do not deviate from the range limited by the above Hammett's $\sigma$ values. Such substituents include the same group as those defined for $X_1$, $X_2$, and $X_3$.

The couplers represented by Formula II may combine together to form a dimer, oligomer or polymer through two or more divalent or more valent group in any one of $R_1$, $X_1$, $X_2$, $X_3$, $Y$, $B_1$, and $B_2$, wherein the number of carbon atom may deviate from the ranges defined for the respective groups.

The following are the examples of the yellow coupler represented by Formula I.

$$Ar_1-COCHCONH-Ar_2$$
$$|$$
$$OAr_3$$

| Coupler No. | $Ar_1$ | $Ar_2$ | $Ar_3$ |
| --- | --- | --- | --- |
| I-1 | 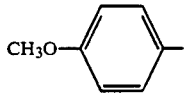 | 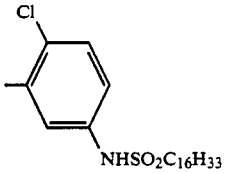 | 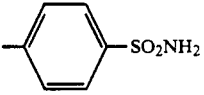 |
| I-2 | 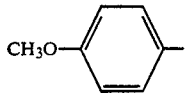 | 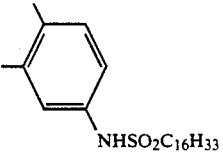 | 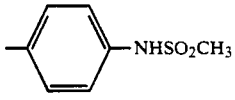 |
| I-3 | 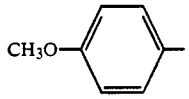 | 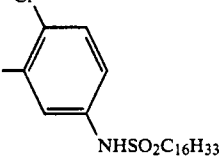 | 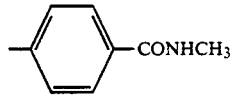 |
| I-4 | 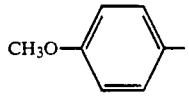 | 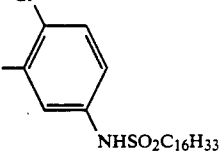 | 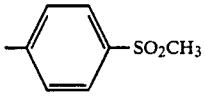 |
| I-5 | 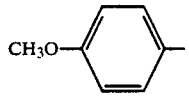 | 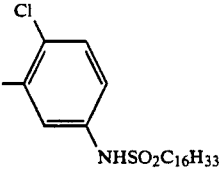 | 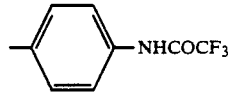 |
| I-6 | 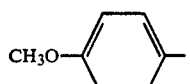 | 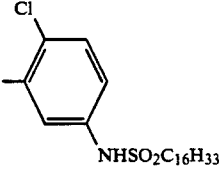 | 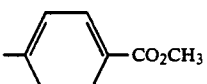 |
| I-7 | 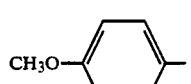 | 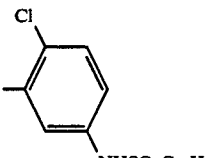 | 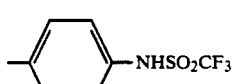 |

-continued $$Ar_1-COCHCONH-Ar_2$$
$$\phantom{Ar_1-COCH}|\phantom{CONH-Ar_2}$$
$$\phantom{Ar_1-CO}OAr_3$$

| Coupler No. | Ar₁ | Ar₂ | Ar₃ |
|---|---|---|---|
| I-8 | CH₃O—C₆H₄— | 4-Cl, 3-(NHSO₂C₁₆H₃₃)—C₆H₃— | 4-(SO₂NHCH₃)—C₆H₄— |
| I-9 | CH₃O—C₆H₄— | 4-Cl, 3-(NHSO₂C₁₆H₃₃)—C₆H₃— | 4-(CONH₂)—C₆H₄— |
| I-10 | CH₃O—C₆H₄— | 4-Cl, 3-(NHSO₂C₁₆H₃₃)—C₆H₃— | 4-(NHCOCH₃)—C₆H₄— |
| I-11 | CH₃O—C₆H₄— | 4-Cl, 3-(NHSO₂C₁₆H₃₃)—C₆H₃— | 4-(SO₂CH₂OH)—C₆H₄— |
| I-12 | CH₃O—C₆H₄— | 4-Cl, 3-(NHSO₂C₁₆H₃₃)—C₆H₃— | 4-(SO₂N(CH₃)₂)—C₆H₄— |
| I-13 | CH₃O—C₆H₄— | 4-Cl, 3-(NHSO₂C₁₆H₃₃)—C₆H₃— | 4-(NHCOC₃F₇)—C₆H₄— |
| I-14 | CH₃O—C₆H₄— | 4-Cl, 3-(NHSO₂C₁₆H₃₃)—C₆H₃— | 4-(NHCO(CH₃)₂CO₂H)—C₆H₄— |
| I-15 | CH₃O—C₆H₄— | 4-Cl, 3-(NHSO₂C₁₆H₃₃)—C₆H₃— | 4-(NHCO(CH₂)₃OH)—C₆H₄— |

-continued $$Ar_1-COCHCONH-Ar_2$$
$$\quad\quad\quad |$$
$$\quad\quad OAr_3$$

| Coupler No. | Ar₁ | Ar₂ | Ar₃ |
|---|---|---|---|
| I-16 | CH₃O—C₆H₄— | 4-Cl, 3-NHSO₂C₁₆H₃₃—C₆H₃— | 4-NHCO(CH₂)₃OCH₃—C₆H₄— |
| I-17 | CH₃O—C₆H₄— | 4-Cl, 3-NHSO₂C₁₆H₃₃—C₆H₃— | 3-NHSO₂CF₃—C₆H₄— |
| I-18 | CH₃O—C₆H₄— | 4-Cl, 3-NHSO₂C₁₆H₃₃—C₆H₃— | 3-NHCOCF₃—C₆H₄— |
| I-19 | CH₃O—C₆H₄— | 4-Cl, 3-NHSO₂C₁₆H₃₃—C₆H₃— | 2-NHSO₂CF₃, 3-OH—C₆H₃— |
| I-20 | CH₃O—C₆H₄— | 4-Cl, 3-NHSO₂C₁₆H₃₃—C₆H₃— | 2-NHSO₂CF₃, 3-NHCOCF₃—C₆H₃— |
| I-21 | C₆H₅— | 4-Cl, 3-NHSO₂C₁₆H₃₃—C₆H₃— | 4-SO₂NH₂—C₆H₄— |
| I-22 | C₆H₅— | 4-Cl, 3-NHSO₂C₁₆H₃₃—C₆H₃— | 4-CO₂H—C₆H₄— |
| I-23 | C₆H₅— | 4-Cl, 3-NHSO₂C₁₆H₃₃—C₆H₃— | 4-NHCOCF₃—C₆H₄— |

-continued $$Ar_1-COCHCONH-Ar_2$$
$$|$$
$$OAr_3$$

| Coupler No. | Ar₁ | Ar₂ | Ar₃ |
|---|---|---|---|
| I-24 | phenyl- | 4-Cl, 3-(NHSO₂C₁₆H₃₃)-phenyl- | -C₆H₄-SO₂NHC₃H₇(i) |
| I-25 | phenyl- | 4-Cl, 3-(NHSO₂C₁₆H₃₃)-phenyl- | -C₆H₄-NHSO₂CH₃ |
| I-26 | phenyl- | 4-Cl, 3-(NHSO₂C₁₆H₃₃)-phenyl- | -C₆H₄-CONHCH₃ |
| I-27 | 2-Cl-phenyl- | 4-Cl, 3-(NHSO₂C₁₆H₃₃)-phenyl- | -C₆H₄-SO₂CH₃ |
| I-28 | 2-Cl-phenyl- | 4-Cl, 3-(NHSO₂C₁₆H₃₃)-phenyl- | -C₆H₄-NHCO(CH₂)₂CO₂H |
| I-29 | 2-Cl-phenyl- | 4-Cl, 3-(NHSO₂C₁₆H₃₃)-phenyl- | -C₆H₄-CO₂CH₃ |
| I-30 | 2-Cl-phenyl- | 4-Cl, 3-(NHSO₂C₁₆H₃₃)-phenyl- | -C₆H₄-NHSO₂C₃H₇(i) |
| I-31 | 3-(CH₃CONH)-phenyl- | 4-Cl, 3-(NHSO₂C₁₆H₃₃)-phenyl- | -C₆H₄-CONH₂ |

-continued $$Ar_1-COCHCONH-Ar_2$$
$$|$$
$$OAr_3$$

| Coupler No. | Ar₁ | Ar₂ | Ar₃ |
|---|---|---|---|
| I-32 | 3-(CH₃CONH)-C₆H₄– | 4-Cl-3-(NHSO₂C₁₆H₃₃)-C₆H₃– | 4-SO₂N(CH₃)₂-C₆H₄– |
| I-33 | 4-CH₃O-2-Cl-C₆H₃– | 4-Cl-3-(NHSO₂C₁₆H₃₃)-C₆H₃– | 4-NHSO₂CH₃-C₆H₄– |
| I-34 | 2-OCH₃-5-NO₂-C₆H₃– | 4-Cl-3-(NHSO₂C₁₆H₃₃)-C₆H₃– | 4-SO₂NH₂-C₆H₄– |
| I-35 | 4-CH₃O-C₆H₄– | 4-Cl-3-(NHSO₂C₁₂H₂₅)-C₆H₃– | 4-SO₂NH₂-C₆H₄– |
| I-36 | 4-CH₃O-C₆H₄– | 4-Cl-3-(NHSO₂C₁₂H₂₅)-C₆H₃– | 4-SO₂CH₃-C₆H₄– |
| I-37 | 4-CH₃O-C₆H₄– | 4-Cl-3-(NHSO₂C₁₂H₂₅)-C₆H₃– | 4-CO₂H-C₆H₄– |
| I-38 | 4-CH₃O-C₆H₄– | 4-Cl-3-(NHSO₂C₁₂H₂₅)-C₆H₃– | 4-CONH₂-C₆H₄– |
| I-39 | 4-CH₃O-C₆H₄– | 4-Cl-3-(NHSO₂C₁₂H₂₅)-C₆H₃– | 4-NHCOCF₃-C₆H₄– |

-continued $$Ar_1-\underset{\underset{OAr_3}{|}}{CO}CHCONH-Ar_2$$

| Coupler No. | Ar₁ | Ar₂ | Ar₃ |
|---|---|---|---|
| I-40 | CH₃O—C₆H₄— | 4-Cl-3-(NHSO₂C₁₂H₂₅)—C₆H₃— | 4-[NHCO(CH₂)₂CO₂H]—C₆H₄— |
| I-41 | CH₃O—C₆H₄— | 4-Cl-3-(NHSO₂C₁₂H₂₅)—C₆H₃— | 4-(NHSO₂CH₃)—C₆H₄— |
| I-42 | CH₃O—C₆H₄— | 4-Cl-3-[NHSO₂CH₂CH(C₆H₁₃)(C₈H₁₇)]—C₆H₃— | 4-[SO₂N(CH₃)₂]—C₆H₄— |
| I-43 | CH₃O—C₆H₄— | 4-Cl-3-[NHSO₂CH₂CH(C₆H₁₃)(C₈H₁₇)]—C₆H₃— | 4-(NHCOCF₃)—C₆H₄— |
| I-44 | C₆H₅— | 4-Cl-3-[NHSO₂CH₂CH(C₆H₁₃)(C₈H₁₇)]—C₆H₃— | 4-(CONHC₂H₅)—C₆H₄— |
| I-45 | CH₃O—C₆H₄— | 4-OCH₃-3-(NHSO₂C₁₆H₃₃)—C₆H₃— | 4-(CONH₂)—C₆H₄— |
| I-46 | CH₃O—C₆H₄— | 4-OCH₃-3-(NHSO₂C₁₆H₃₃)—C₆H₃— | 4-(NHSO₂CF₃)—C₆H₄— |

$$Ar_1-COCHCONH-Ar_2$$
$$|$$
$$OAr_3$$

| Coupler No. | Ar₁ | Ar₂ | Ar₃ |
|---|---|---|---|
| I-47 | 4-CH₃O-C₆H₄- | 4-OCH₃, 3-CH₃, (NHSO₂C₁₂H₂₅ at another position)-C₆H₂- | 4-CO₂H-C₆H₄- |
| I-48 | 4-CH₃O-C₆H₄- | 4-Cl, 3-CH₃, 5-(NHSO₂-cyclohexyl-C₄H₉(t))-C₆H₂- | 4-NHCO(CH₂)₃OCH₃-C₆H₄- |
| I-49 | C₆H₅- | 4-Cl, 3-CH₃, 5-(NHSO₂C₁₂H₂₅)-C₆H₂- | 4-NHCO(CH₂)₂CO₂H-C₆H₄- |

The following are the examples of the yellow coupler represented by Formula II.

$$Ar_1-COCHCONH-Ar_2$$
$$|$$
$$OAr_3$$

| Coupler No. | Ar₁ | Ar₂ | Ar₃ |
|---|---|---|---|
| II-1 | 4-CH₃O-C₆H₄- | 4-Cl, 3-CH₃, 5-(NHSO₂C₁₆H₃₃)-C₆H₂- | 4-NO₂-C₆H₄- |
| II-2 | 4-CH₃O-C₆H₄- | 4-Cl, 3-CH₃, 5-(NHSO₂C₁₆H₃₃)-C₆H₂- | 4-(SO₂-C₆H₅)-C₆H₄- |
| II-3 | 4-CH₃O-C₆H₄- | 4-Cl, 3-CH₃, 5-(NHSO₂C₁₆H₃₃)-C₆H₂- | 4-(CH=CHCO₂H)-C₆H₄- |
| II-4 | 4-CH₃O-C₆H₄- | 4-Cl, 3-CH₃, 5-(NHSO₂C₁₆H₃₃)-C₆H₂- | 4-(CH=C(CN)₂)-C₆H₄- |

-continued $$Ar_1-COCHCONH-Ar_2$$
$$|$$
$$OAr_3$$

| Coupler No. | Ar₁ | Ar₂ | Ar₃ |
|---|---|---|---|
| II-5 | CH₃O—C₆H₄— | 4-Cl, 3-(NHSO₂C₁₆H₃₃)-C₆H₃— | 3,5-diCl-C₆H₃— |
| II-6 | CH₃O—C₆H₄— | 4-Cl, 3-(NHSO₂C₁₆H₃₃)-C₆H₃— | 4-(4-HO-C₆H₄-SO₂)-C₆H₄— |
| II-7 | CH₃O—C₆H₄— | 4-Cl, 3-(NHSO₂C₁₆H₃₃)-C₆H₃— | 3-NO₂, 4-OCH₃-C₆H₃— |
| II-8 | CH₃O—C₆H₄— | 4-Cl, 3-(NHSO₂C₁₆H₃₃)-C₆H₃— | 3-NO₂-C₆H₄— |
| II-9 | CH₃O—C₆H₄— | 4-Cl, 3-(NHSO₂C₁₆H₃₃)-C₆H₃— | 4-(α-Br-β-CO₂H-vinyl)-C₆H₄— |
| II-10 | CH₃O—C₆H₄— | 4-Cl, 3-(NHSO₂C₁₆H₃₃)-C₆H₃— | 2-SO₂CH₃, 3-Cl-C₆H₃— |
| II-11 | CH₃O—C₆H₄— | 4-Cl, 3-(NHSO₂C₁₆H₃₃)-C₆H₃— | 4-SO₂CF₃-C₆H₄— |
| II-12 | CH₃O—C₆H₄— | 4-Cl, 3-(NHSO₂C₁₆H₃₃)-C₆H₃— | 2,3-(—CF₂—O—CF₂—)-C₆H₃— |

-continued $$Ar_1-COCHCONH-Ar_2$$
$$\phantom{Ar_1-COCHCO}|\phantom{NH-Ar_2}$$
$$\phantom{Ar_1-COC}OAr_3$$

| Coupler No. | Ar₁ | Ar₂ | Ar₃ |
|---|---|---|---|
| II-13 | 4-CH₃O-C₆H₄- | 4-Cl, 3-(NHSO₂C₁₆H₃₃)-C₆H₃- | 2-NO₂, 4-CO₂CH₃-C₆H₃- |
| II-14 | 4-CH₃O-C₆H₄- | 4-Cl, 3-(NHSO₂C₁₆H₃₃)-C₆H₃- | 3,4,5-trichlorophenyl |
| II-15 | C₆H₅- | 4-Cl, 3-(NHSO₂C₁₆H₃₃)-C₆H₃- | 4-NO₂-C₆H₄- |
| II-16 | C₆H₅- | 4-Cl, 3-(NHSO₂C₁₆H₃₃)-C₆H₃- | 4-(4-hydroxyphenylsulfonyl)phenyl |
| II-17 | C₆H₅- | 4-Cl, 3-(NHSO₂C₁₆H₃₃)-C₆H₃- | 3,5-bis(CF₃)-C₆H₃- |
| II-18 | C₆H₅- | 4-Cl, 3-(NHSO₂C₁₆H₃₃)-C₆H₃- | 4-(SO₂CF₃)-C₆H₄- |
| II-19 | 3-(CH₃CONH)-C₆H₄- | 4-Cl, 3-(NHSO₂C₁₆H₃₃)-C₆H₃- | 4-NO₂-C₆H₄- |
| II-20 | 3-(CH₃CONH)-C₆H₄- | 4-Cl, 3-(NHSO₂C₁₆H₃₃)-C₆H₃- | 4-(phenylsulfonyl)phenyl |

-continued $$Ar_1-COCHCONH-Ar_2$$
$$|$$
$$OAr_3$$

| Coupler No. | Ar₁ | Ar₂ | Ar₃ |
|---|---|---|---|
| II-21 | 4-CH₃O-C₆H₄- | 4-Cl-3-methyl-5-(NHSO₂C₁₂H₂₅)-phenyl | 4-(C₆H₅SO₂)-C₆H₄- |
| II-22 | C₆H₅- | 4-Cl-3-methyl-5-(NHSO₂C₁₂H₂₅)-phenyl | 4-NO₂-C₆H₄- |
| II-23 | C₆H₅- | 4-Cl-3-methyl-5-(NHSO₂C₁₂H₂₅)-phenyl | 4-(C₆H₅SO₂)-C₆H₄- |
| II-24 | C₆H₅- | 4-Cl-3-methyl-5-(NHSO₂CH₂CH(C₂H₅)C₄H₉)-phenyl | 4-(C₆H₅SO₂)-C₆H₄- |
| II-25 | 4-CH₃O-C₆H₄- | 4-Cl-3-methyl-5-(NHSO₂CH₂CH(C₆H₁₃)C₈H₁₇)-phenyl | 4-NO₂-C₆H₄- |
| II-26 | 4-CH₃O-C₆H₄- | 4-Cl-3-methyl-5-(NHSO₂-trans-4-(t-C₄H₉)cyclohexyl)-phenyl | 4-NO₂-C₆H₄- |
| II-27 | 4-CH₃O-C₆H₄- | 4-CH₃O-3-methyl-5-(NHSO₂C₁₆H₃₃)-phenyl | 4-NO₂-C₆H₄- |
| II-28 | 4-CH₃O-C₆H₄- | 4-CH₃O-3-methyl-5-(NHSO₂C₁₆H₃₃)-phenyl | 4-(4-HO-C₆H₄-SO₂)-C₆H₄- |

-continued $$Ar_1-COCHCONH-Ar_2$$
$$|$$
$$OAr_3$$

| Coupler No. | Ar₁ | Ar₂ | Ar₃ |
|---|---|---|---|
| II-29 | 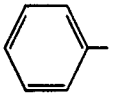 | 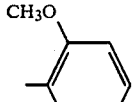 CH₃O– , –NHSO₂C₁₆H₃₃ | 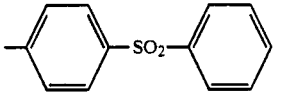 –⟨⟩–SO₂–⟨⟩ |
| II-30 | 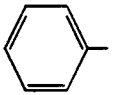 | CH₃O– , –NHSO₂CH₂CH(C₆H₁₃)(C₈H₁₇) | 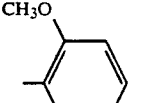 –⟨⟩–NO₂ |
| II-31 | CH₃O–⟨⟩– | CH₃O– , –NHSO₂CH₂CH(C₆H₁₃)(C₈H₁₇) | 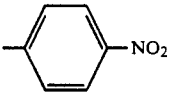 2,5-diCl-phenyl |
| II-32 | CH₃O–⟨⟩– | Cl– , –NHSO₂CH₂C(CH₃)₂C₆H₁₃ | –⟨⟩–NO₂ |

The following are the Synthesis examples of the above couplers.

SYNTHESIS EXAMPLE 1

(Synthesis of Exemplified Coupler I-1)

There were dissolved in 100 ml of acetonitrile, 6.4 grams of α-chloro-α-(4-methoxybenzoyl)-2-chloro-5-hexadecylsulfonylaminoacetanilide, 1.9 g of p-hydroxybenzenesulfonamide and 1.1 g of triethylamine, and the solution was heated at about 60° C. for 3 hours. After completion of the reaction, the solvent was removed under reduced pressure, and the residue was dissolved in 200 ml of ethyl acetate and washed each twice by a 30% hydrochloric acid solution and a 5% potassium hydrogencarbonate solution. After washing, an organic phase was separated and dried by magnesium sulfate. Then, the solvent was removed under reduced pressure. The residue was recrystallized from 25 ml of ethanol, thereby obtaining 5.4 g of the exemplified coupler I-1 (yield 70%).

SYNTHESIS EXAMPLE 2

(Synthesis of Exemplified Coupler I-6)

There were dissolved, in 100 ml of acetone, 6.4 grams of α-chloro-α-(4-methoxybenzoyl)-2-chloro-5-hexadecylsulfonylaminoacetanilide and 1.9 g of potassium 4-methoxycarbonylphenoxide, and the solution was refluxed for one hour. After refluxing, the reaction product was treated in the same procedure as in synthesis example 1, whereby 3.2 g of the exemplified coupler I-6 were obtained. (yield 42%). M.P. 125° to 129° C.

SYNTHESIS EXAMPLE 3

(Synthesis of exemplified coupler II-1)

There were dissolved in 100 ml of acetone, 6.4 g of α-chloro-α-(4-methoxybenzoyl)-2-chloro-5-hexadecylsulfonylaminoacetaonilide and 1.9 g of potassium 4-nitrophenoxide, and the solution was refluxed for one hour.

Then, acetone was distilled off under reduced pressure, and the residue was dissolved in 200 ml of ethyl acetate. The solution was washed three times with 100 ml of an aqueous 5% potassium hydrogen carbonate solution and then once with 100 ml of saturated brine. After washing, an organic layer was separated and dried with magnesium sulfate to remove the solvent under reduced pressure. The residue was recrystallized with 30 ml of ethanol, whereby 5.2 g of exemplified coupler II-1 was obtained (70% yield). The melting point was 87° to 89° C.

SYNTHESIS EXAMPLE 4

(Synthesis of exemplified coupler II-6)

There were dissolved in 100 ml of acetonitrile, 6.4 g of α-chloro-α-(4-methoxybenzoyl)-2-chloro-5-hexadecylsulfonylaminoacetanilide, 5.0 g of bis(4-hydroxyphenyl)sulfone, and 1.1 g of triethylamine, and the solution was heated at 60° C. for 3 hours. After completing the reaction, the reaction product was treated in the same manner as in Synthesis Example 3, whereby 4.4 g of exemplified coupler II-6 was obtained (52% yield).

The chemical structures of the above synthesized couplers were confirmed by an NMR spectrum, an IR spectrum and a mass spectrum.

Other couplers of the invention were also synthesized likewise starting from corresponding materials in accordance with the procedures described for synthesis examples 1 to 4.

The yellow couplers of the invention may be used alone or in combination, and may also be used in combination with any known pivaloylacetanilide type or benzoylacetanilide type yellow couplers.

The yellow coupler of the invention can be used as a so-called protect-dispersion type coupler, which is dissolved in a high boiling organic solvent hardly miscible with water and having a boiling point of not lower than 175° C., such as dibutyl phthalate and tricresyl phosphate. Further, instead of the above high boiling organic solvent, the coupler may be dissolved in a substantially water-insoluble low boiling organic solvent such as ethyl acetate and butyl acetate, or in a water-soluble low boiling organic solvent such as methanol, ethanol, methyl cellosolve and methyl isobutyl ketone. The coupler of the invention may also be used as a coupler for a so-called diffusion transfer process, in which a light-sensitive element having a light-sensitive layer is contacted with a processing sheet to thereby form a transfer image on an image-receiving layer of an image-receiving element.

The yellow coupler of the invention can be applied to any of the dye image forming methods described in Japanese Patent Examined Publication No. 26585/1974, U.S. Pat. No. 3,486,890 and Research Disclosure Nos. 12044 and 12840, in which a light-sensitive material containing the yellow coupler of the invention and an aromatic primary amine developing agent or a precursor thereof is exposed imagewise and then developed by an alkali treatment or a heat treatment, whereby a dye image with an excellent gradation can be obtained.

The color developing agent used in the invention is an aromatic primary amine compound typified by p-aminophenol and p-phenylenediamine compounds including p-aminophenol, diethyl-p-phenylenediamine hydrochloride, monomethyl-p-phenylenediamine hydrochloride, dimethyl-p-phenylenediamine hydrochloride, 2-amino-5-diethylaminotoluene hydrochloride, 2-amino-5-(N-ethyl-N-dodecylamino)-toluene, N-ethyl-N-β-methanesulfonamideethyl-3-methyl-4-aminoaniline sulfate, N-ethyl-N-β-methanesulfonamideethyl-4-aminoaniline, 4-N-ethyl-N-β-hydroxyethylaminoaniline, N-ethyl-N-β-methoxyethyl-3-methyl-4-aminoaniline p-toluenesulfonate, N-ethyl-N-[2-(2-methoxyethoxy)ethyl]-3-methyl-4-aminoaniline p-toluenesulfonate, and N-ethyl-N-{2-[2-(2-methoxyethoxy)ethoxy]ethyl}-3-methyl-4-aminoaniline p-toluenesulfonate, The invention can be applied to such a variety of color photographic light-sensitive materials as sensitive to electromagnetic wave energy such as ultraviolet ray, visible ray, infrared ray, X-ray, X-ray and microwave.

The above color developing agents may be used alone or in combination. In the invention, there may be contained in a developer containing conventional additives including an alkali agent such as sodium hydroxide, sodium carbonate and potassium carbonate, alkali metal sulfite, alkali metal bisulfite, alkali metal thiocyanate, alkali metal halide, benzyl alcohol, a water softener, a thickener; and a development adjusting agent such as citrazine.

The color developer has a pH value of 7 or higher, and preferably 10 to 13.

A color developer in the invention may be used in combination with a black-and-white developer. The black-and-white developer is a black-and-white first developer used for processing conventional silver halide color photographic light-sensitive materials, or one used for processing a black-and-white photographic light-sensitive material, and may contain well-known various additives added to a black-and-white developer, including a developing agent such as 1-phenyl-3-pyrazolidone, Metol and hydroquinone; a preservative such as a sulfite; a development accelerator such as sodium hydroxide, sodium carbonate and potassium carbonate; an inorganic or organic development inhibitor such as potassium bromide, 2-methylbenzimidazole and methylbenzothiazole; a water softener such as a polyphosphate; and a surface overdevelopment inhibitor comprising a slight amount of an iodide and a mercapto compound.

In the invention, the development is followed by bleaching, fixing or bleach-fixing, stabilizing, washing and stopping.

A bleaching agent for a bleaching or bleach-fixing bath is preferably a metallic complex of aminopolycarboxylic acid such as ferric ethylenediaminetetraacetate, and/or a metallic complex of a polycarboxylic acid. The color developing may be made more than twice, for example, the first developing and the second developing.

The yellow coupler of the invention can be incorporated into a color photographic light-sensitive material by conventional methods. For example, as mentioned above, the yellow couplers of the invention can be incorporated singly or in combination into the photographic material by the protect dispersion method, in which the couplers are dissolved in a single solvent or a mixture of a high boiling Organic solvent with a boiling point of not lower than 175° C., such as tricresyl phosphate and dibutyl phthalate, and a low boiling organic solvent such as ethyl acetate and butyl propionate, and then the solution is mixed with a gelatin solution containing a surface active agent. The mixture is dispersed in an emulsion by a high-speed rotary mixer or a colloid mill and directly incorporated into a silver halide emulsion, which is then coated on a support and dried, or the above emulsion is set and cut into noodle-like pieces, followed by washing to remove the low boiling solvent therefrom, and then added to an emulsion, which is then coated on a support and dried. The yellow coupler of the invention is added in an amount of preferably 10 to 300 g per mole of silver halide.

The silver halide photographic light-sensitive material used in the invention may be of any type for any use. Especially, it can be applied preferably to a multilayer color photographic light-sensitive materials for a negative, color print and a color reversal. The silver halides used for these light-sensitive materials include silver chloride, silver bromide, silver iodide, silver chlorobromide, silver iodobromide and silver chloroiodobromide. A silver halide emulsion may be prepared by any conventional method. The silver halide emulsion may be of any type including a so-called conversion emulsion, a lippmann emulsion, a covered grain emulsion, or an optically or chemically prefogged emulsion. An appropriate emulsion is selected by application. The silver halide may be chemically sensitized singly or combinedly by active gelatin; sulfur sensitizers such as ally thiocarbamide, thiourea, cystine; selenium sensitizers; reduction sensitizers such as a stannous salt and polyamine; noble metal sensitizers including gold sensitizers such as potassium aurithiocyanate, potassium chloroaurate, 2-aurosulfobenzothiazolemethochloride, and sensitizers of water-soluble salts of ruthenium, rhodium and iridium, such as ammonium chloropalladate, potassium chloroplatinate and sodium chloropalladate.

Further, the silver halide may be subjected to spectral sensitization (e.g., for supersensitization) to a prescribed wavelength region by single or combined use of spectral sensitizers including cyanine dyes and merocyanine dyes, such as zeromethine dyes, monomethine dyes, dimethine dyes and trimethine dyes.

The silver halide is dispersed in a protective colloid.

Alkali-treated gelatin is generally used as the protective colloid used for forming layers including light-sensitive layers and others such as an intermediate layer, a protective layer and a filter layer, and there may be used singly or in combination acid-treated gelatin, gelatin derivatives, colloidal albumin, cellulose derivatives, and synthetic resins including polyvinyl compounds such as polyvinyl alcohol. Further, acetyl cellulose containing 19 to 26% acetyl and a water-soluble ethanolaminecellulose acetate may also be used in combination.

The silver halide photographic light-sensitive material of the invention may contain other color couplers together with the yellow coupler of the invention in order to form a multicolor image. The examples thereof include 5-pyrazolone magenta couplers and phenol or naphthol cyan couplers. There may also be used in combination therewith azo colored couplers for automasking, osazone couplers and diffusible dye-releasing couplers. It is preferable to use colorless couplers, which are colorless before color developing, in combination with the above masking couplers. In addition, in order to improve photographic characteristics, the light-sensitive material of the invention may also contain various other couplers such as competing couplers, DIR couplers and BAR (bleach accelerator releasing) couplers.

The magenta coupler usable in combination with the yellow coupler of the invention includes pyrazolone, pyrazotriazole, pyrazolinobenzimidazole and indazolone compounds.

The cyan coupler usable in combination with the yellow coupler of the invention includes phenol compounds, active site-ortho-aryl-substituted naphthol compounds, and naphthol compounds.

The silver halide emulsion containing the yellow coupler of the invention is coated on a support provided with a subbing layer, an intermediate layer, a filter layer, an anticurl layer and a protective layer according to necessity, whereby a silver halide photographic light-sensitive material of the invention is prepared. The support usable in the invention includes a film and a sheet made of paper, polyethylene-laminated paper, glass, cellulose acetate, cellulose nitrate, polyester, polycarbonate, polyamide, polystyrene and polyolefin. The support may, in order to improve its adherence to the layers, be subjected to surface treatment such as various hydrophilicity treatments including saponification treatment, corona-discharge treatment, subbing treatment and setting treatment.

The silver halide photographic light-sensitive material of the invention comprises basically at least a support and a light-sensitive layer provided thereon and generally comprises several layers provided to various positions according to purposes. The light-sensitive layer itself may be of a multilayer construction composed of a layer containing a relatively high sensitive silver halide and one containing a relatively low sensitive silver halide, each spectrally sensitized to the same wavelength region or to different wavelength regions.

The silver halide photographic light-sensitive material of the invention may contain photographic additives in the light-sensitive layers and other component layers such as an intermediate layer, a subbing layer, a filter layer, a protective layer, and an image receiving layer. The photographic additives include a stabilizer such as a mercury compound, triazole, azaindene, quaternary benzothiazolium, a zinc salt and a cadmium salt; a sensitizer such as a quaternary ammonium salt and polyethylene glycol; a physical property improving agent such as glycerol, dihydroxyalkane including 1,5-pentane- diol, ethylenebisglycolic acid ester, bisethoxydiethyleneglycol succinate, acrylic amide, and an emulsion polymer; a hardener such as formaldehyde, halogen-substituted fatty acid including mucochloric acid and mucobromic acid, a compound having an acid anhydride group, dicarboxylic acid chloride, disulfonic acid chloride, methanesulfonic acid diester, a sodium bisulfite derivative of dialdehyde in which the aldehyde groups are separated by 2 or 3 carbon atoms, bisaziridine, and ethyleneimine; a spreading agent such as saponin, lauryl or oleyl monoether of polyethylene glycol, a sulfated or alkylated polyethylene glycol derivative; a coating aid such as sulfosuccinate; an organic solvent including a coupler solvent such as a high boiling organic solvent and a low boiling solvent, including dibutyl phthalate, tricresyl phosphate, acetone, methanol, ethanol, and ethyl cellosolve; a DIR compound which releases a color development inhibitor in color developing and produces a substantially colorless compound; and others including an antistatic agent, a defoaming agent, an ultraviolet absorbing agent, a brightening agent, an antislip agent, a matting agent, an antihalation agent, and an antiirradiation agent. These additives may be used alone or in combination.

The silver halide photographic light-sensitive material containing the yellow coupler of the invention may contain an ultraviolet absorbing agent to further improve the fastness of the formed yellow image.

EXAMPLES

The present invention is explained in further detail by the following examples.

The following couplers were used for comparison.

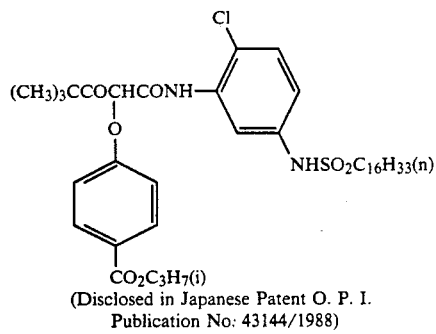

Y-1

(Disclosed in Japanese Patent O. P. I.
Publication No. 43144/1988)

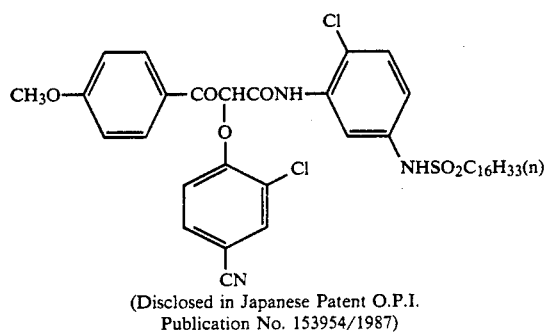

Y-2

(Disclosed in Japanese Patent O.P.I.
Publication No. 153954/1987)

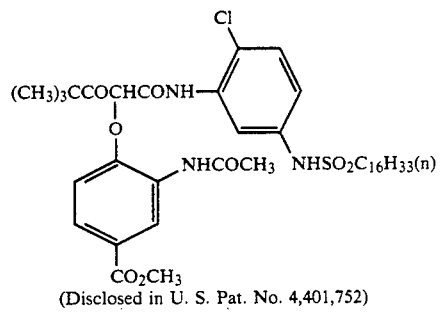

Y-3

(Disclosed in U. S. Pat. No. 4,401,752)

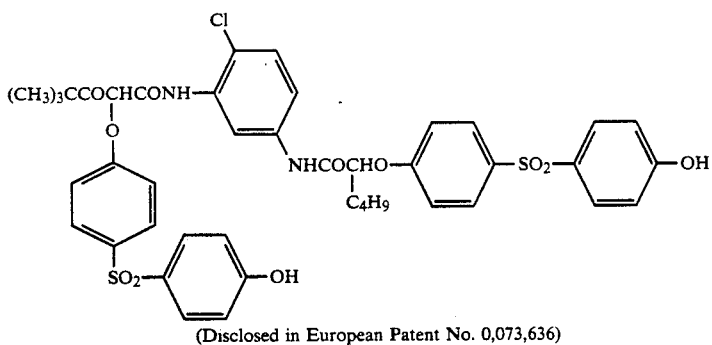

Y-4

(Disclosed in European Patent No. 0,073,636)

EXAMPLE 1

As is shown in Table 1, each 10.0 g of the yellow coupler of the invention (indicated with exemplified coupler Nos.) and the above comparative coupler were added to a mixture of 2.0 ml of dibutyl phthalate and 20 ml of ethyl acetate, and dissolved by heating to 50° C.

The solution was mixed with 5 ml of a 10% aqueous solution of Alkanol B (alkylnaphthalene sulfonate, produced by DuPont) and 100 ml of a 5% gelatin aqueous solution, and the mixture was emulsified several times by passing through a colloid mill. The emulsion was allowed to stand at 20° C. for 48 hours, and then visually observed with a microscope.

The results are shown in Table 1.

TABLE 1

| Sample No. | Coupler No. | Condition after standing |
| --- | --- | --- |
| 1 (Invention) | I-2 | No deposition |
| 2 (Invention) | I-3 | " |
| 3 (Invention) | I-12 | " |
| 4 (Invention) | I-16 | " |
| 5 (Invention) | I-24 | " |
| 6 (Invention) | I-36 | " |
| 7 (Invention) | I-43 | " |
| 8 (Invention) | I-48 | " |
| 9 (Comparative) | Y-1 | " |
| 10 (Comparative) | Y-2 | Slight deposition |
| 11 (Comparative) | Y-3 | Remarkable deposition |

TABLE 1-continued

| Sample No. | Coupler No. | Condition after standing |
|---|---|---|
| 12 (Comparative) | Y-4 | Slight deposition |

As is apparent from Table 1, any of the yellow couplers of the invention shows no deposition, and has an excellent aging stability in an emulsion.

EXAMPLE 2

There were coated the following 7 layers in sequence on a support laminated with polyethylene on both sides after subjected to corona dicharge to thereby prepare a multilayer color photographic paper. Sample No. 13.

The coated amount of each component is a weight per m² unless otherwise stated.

Layer 1: A layer containing 1.5 g of gelatin, 0.33 g (silver equivalent) of a blue-sensitive silver chlorobromide emulsion (85 mole % silver bromide, average grain size 0.65 μm) and 0.2 μg of dioctyl phthalate dissolving $1.1 \times 10^{-3}$ mole of exemplified yellow coupler I-1 and 0.015 g of the following compound HQ-1.

Layer 2: A layer containing 1.0 g of gelatin and 0.06 g of dioctyl phthalate dissolving 0.09 g of HQ-1.

Layer 3: A layer containing 1.3 g of gelatin, 0.27 g (silver equivalent) of a green-sensitive silver chlorobromide emulsion (50 mole % silver bromide, average grain size 0.45 μm), 0.2 g of dioctyl phthalate dissolving $0.59 \times 10^{-3}$ mole of the following magenta coupler M-1 and 0.015 g of HQ-1, and 0.15 g of the following antiirradiation dye AID-1.

Layer 4: A layer containing 1.5 g of gelatin, 0.8 g of ultraviolet absorbing agent UV-1 and 0.6 g of dioctyl phthalate dissolving 0.04 g of HQ-1.

Layer 5: A layer containing 1.3 g of gelatin, 0.3 g (silver equivalent) of a red-sensitive silver chlorobromide emulsion (50 mole % silver bromide, average grain size 0.35 μm) and 0.2 g of dioctyl phthalate dissolving $0.75 \times 10^{-3}$ mole of the following cyan coupler C-1 and 0.005 g of HQ-1.

Layer 6: A layer containing 1.0 g of gelatin, 0.4 g of ultraviolet absorbing agent and 0.015 g of dioctyl phthalate dissolving 0.01 g of HQ-1.

Layer 7: A layer containing 1.0 g of gelatin and 0.015 g of the following filter dye AID-2.

The respective emulsions containing the couplers were used after kept at 40° C. for 8 hours.

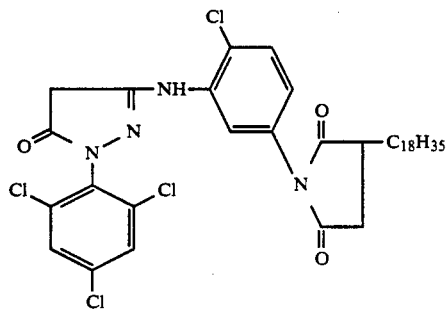

M-1

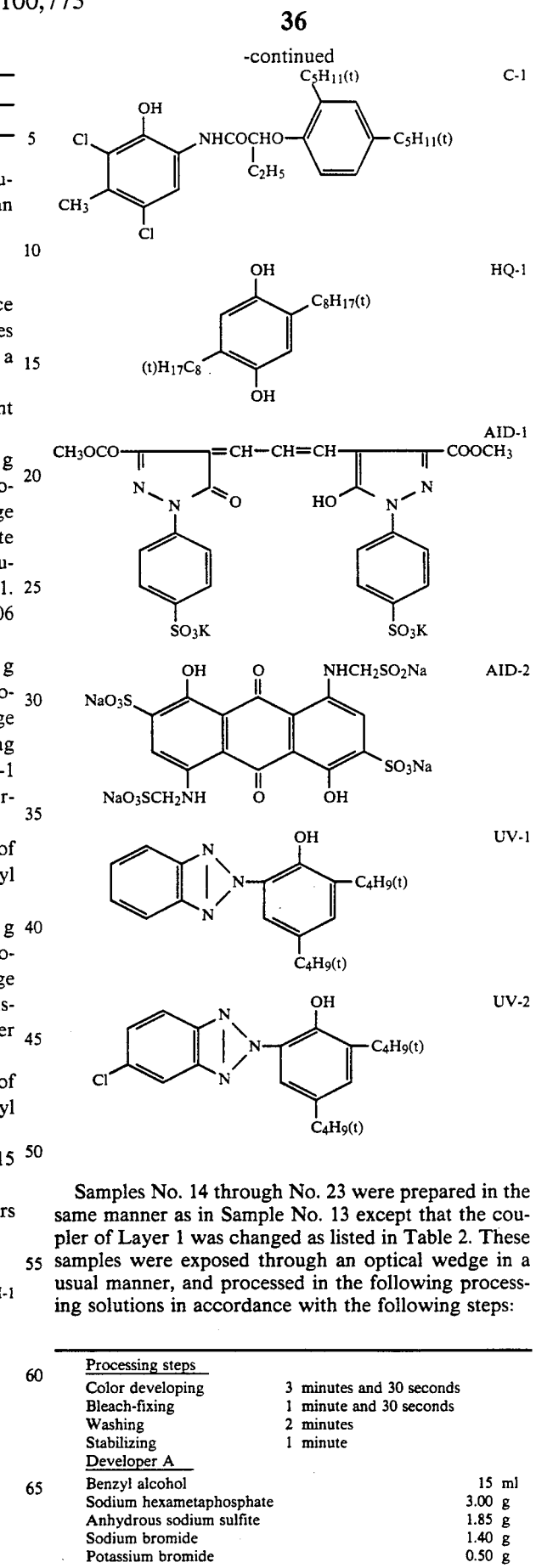

Samples No. 14 through No. 23 were prepared in the same manner as in Sample No. 13 except that the coupler of Layer 1 was changed as listed in Table 2. These samples were exposed through an optical wedge in a usual manner, and processed in the following processing solutions in accordance with the following steps:

| Processing steps | |
|---|---|
| Color developing | 3 minutes and 30 seconds |
| Bleach-fixing | 1 minute and 30 seconds |
| Washing | 2 minutes |
| Stabilizing | 1 minute |
| Developer A | |
| Benzyl alcohol | 15 ml |
| Sodium hexametaphosphate | 3.00 g |
| Anhydrous sodium sulfite | 1.85 g |
| Sodium bromide | 1.40 g |
| Potassium bromide | 0.50 g |

-continued

| | |
|---|---|
| Boric acid (Na₂B₄O₇.10H₂O) | 39.10 g |
| N-ethyl-N-[2-(methanesulfonamidoethyl)]-3-methyl-4-aminoaniline sulfate | 4.50 g |
| Water was added to make total quantity 1 liter. | |
| pH was adjusted to 10.3 with sodium hydroxide. | |

Developer B

Prepared in the same manner as in Developer A except that benzyl alcohol was excluded.

| Bleach-fixer | |
|---|---|
| Ferric-ammonium ethylenediaminetetraacetate | 61.0 g |
| Diammonium ethylenediaminetetraacetate | 5.0 g |
| Ammonium thiosulfate | 124.5 g |
| Sodium metabisulfite | 13.3 g |
| Sodium bisulfite | 2.7 g |
| Water was added to make total quantity 1 liter, and pH was adjusted to 6.5. | |
| Stabilizer | |
| Glacial acetic acid (trihydrated) | 20 ml |

Pure water of 800 ml was added, and pH was adjusted to 3.5 to 4.0 with acetic acid trihydrate. The whole quantity was adjusted to 1 liter.

The evaluation results of the dye images obtained by processing are given in Table 2.

TABLE 2

| | | Maximum density | | | | | |
|---|---|---|---|---|---|---|---|
| | Coup- | Developer A | | | Developer B | | |
| Sample No. | ler No. | Yellow | Magenta | Cyan | Yellow | Magenta | Cyan |
| 13 (Inv) | I-1 | 2.44 | 2.63 | 2.60 | 2.36 | 2.54 | 2.36 |
| 14 (Inv) | I-2 | 2.46 | 2.60 | 2.57 | 2.38 | 2.52 | 2.37 |
| 15 (Inv) | I-3 | 2.45 | 2.62 | 2.56 | 2.40 | 2.55 | 2.35 |
| 16 (Inv) | I-14 | 2.48 | 2.61 | 2.59 | 2.39 | 2.51 | 2.38 |
| 17 (Inv) | I-24 | 2.47 | 2.63 | 2.61 | 2.41 | 2.53 | 2.37 |
| 18 (Inv) | I-36 | 2.45 | 2.63 | 2.59 | 2.36 | 2.54 | 2.36 |
| 19 (Inv) | I-43 | 2.46 | 2.59 | 2.58 | 2.35 | 2.56 | 2.34 |
| 20 (Com) | Y-1 | 1.98 | 2.60 | 2.60 | 1.78 | 2.55 | 2.39 |
| 21 (Com) | Y-2 | 2.36 | 2.61 | 2.62 | 2.22 | 2.51 | 2.35 |
| 22 (Com) | Y-3 | 2.12 | 2.62 | 2.58 | 2.00 | 2.50 | 2.38 |
| 23 (Com) | Y-4 | 1.89 | 2.62 | 2.60 | 1.72 | 2.53 | 2.36 |

As is apparent from Table 2, the samples containing the yellow couplers of the invention show less drop of the maximum densities and better color balance than the samples containing the comparative yellow couplers even where processed in the developer B with no benzyl alcohol.

EXAMPLE 3

There were provided the layers of the following compositions in sequence on a triacetyl cellulose film support to thereby prepare a multilayer color photographic light-sensitive material, Sample No. 24.

Layer 1: Antihalation layer (HC-1)

A gelatin layer containing black colloidal silver.

Layer 2: Intermediate layer (I.L.)

A gelatin layer containing emulsified 2,5-di-t-octylhydroquinone

Layer 3: Low-speed red-sensitive silver halide emulsion layer (RL-1)

A monodispersed emulsion comprising AgBrI: 6 mole % AgI, average grain size 0.30 μm (EM-I), coated silver 1.8 g/m²,

| | |
|---|---|
| Sensitizing dye I | $6 \times 10^{-5}$ mol per mol of silver |
| Sensitizing dye II | $1.0 \times 10^{-5}$ mol per mol of silver |
| Cyan coupler C-2 | 0.06 mol per mol of silver |
| Colored cyan coupler CC-1 | 0.003 mol per mol of silver |
| DIR compound D-1 | 0.0015 mol per mol of silver |
| DIR compound D-2 | 0.002 mol per mol of silver |

Layer 4: High-speed red-sensitive silver halide emulsion layer (RH-1)

A monodispersed emulsion comprising AgBrI: 7 mol % AgI, average grain size 0.5 μm (EM-II), coated silver 1.3 g/m²,

| | |
|---|---|
| Sensitizing dye I | $3 \times 10^{-5}$ mol per mol of silver |
| Sensitizing dye II | $1.0 \times 10^{-5}$ mol per mol of silver |
| Cyan coupler C-2 | 0.02 mol per mol of silver |
| Colored cyan coupler CC-1 | 0.0015 mol per mol of silver |
| DIR compound D-2 | 0.001 mol per mol of silver |

Layer 5: Intermediate layer (I.L.)

The same gelatin layer as Layer 2.

Layer 6: Low-speed green-sensitive silver halide emulsion layer (GL-1)

Em-1, coated silver 1.5 g/m²,

| | |
|---|---|
| Sensitizing dye III | $2.5 \times 10^{-5}$ mol per mol of silver |
| Sensitizing dye IV | $1.2 \times 10^{-5}$ mol per mol of silver |
| Magenta coupler M-2 | 0.050 mol per mol of silver |
| Colored magenta coupler CM-1 | 0.009 mol per mol of silver |
| DIR compound D-1 | 0.0010 mol per mol of silver |
| DIR compound D-3 | 0.0030 mol per mol of silver |

Layer 7: High-speed green-sensitive silver halide emulsion layer (GH-1)

Em-II, coated silver 1.4 g/m²,

| | |
|---|---|
| Sensitizing dye III | $1.5 \times 10^{-5}$ mol per mol of silver |
| Sensitizing dye IV | $1.0 \times 10^{-5}$ mol per mol of silver |
| Magenta coupler M-2 | 0.020 mol per mol of silver |
| Colored magenta coupler CM-1 | 0.002 mol per mol of silver |
| DIR compound D-3 | 0.0010 mol per mol of silver |

Layer 8: Yellow filter layer (YC-1)

A gelatin layer containing yellow colloidal silver and emulsified 2,5-di-t-octyl hydroquinone.

Layer 9: Low-speed blue-sensitive silver halide emulsion layer (BL-1)

A monodispersed emulsion comprising AgBrI: 6 mol % AgI, average grain size 0.48 μm (EM-III), coated silver 0.9 g/m²,

| | |
|---|---|
| Sensitizing dye V | $1.3 \times 10^{-5}$ mol per mol of silver |

-continued

| | |
|---|---|
| Comparative yellow coupler Y-1 | 0.29 mol per mol of silver |
| Tricresyl phosphate | 0.7 ml/m² |

Layer 10: High-speed blue-sensitive silver halide emulsion layer (BH-1)

A monodispersed emulsion comprising AgBrI: 15 mol % AgI, average grain size 0.8 μm (EM-IV), coated silver 0.5 g/m²,

| | |
|---|---|
| Sensitizing dye V | $1.0 \times 10^{-5}$ mol per mol of silver |
| Comparative yellow coupler Y-1 | 0.08 mol per mol of silver |
| DIR compound D-2 | 0.0015 mol per mol of silver |
| Tricresyl phosphate | 0.2 ml/m² |

Layer 11: First protective layer (Pro-1)

A gelatin layer containing silver bromoiodide (1 mol % AgI, average grain size 0.07 μm), coated silver 0.5 g/m², and UV absorbers UV-3 and UV-4.

Layer 12: Second protective layer (Pro-2)

A gelatin layer containing polymethyl methacrylate particles (diameter 1.5 μm) and formalin scavenger HS-1.

Besides the above components, each of the layers contains a hardener H-1 and a surface active agent.

The following compounds are contained in the layers of Sample No. 24:

Sensitizing dye I: Anhydro-5,5'-dichloro-9-ethyl-3,3'-di-(3-sulfopropyl)thiacarbocyanine hydroxide Sensitizing dye II: Anhydro-9-ethyl-3,3'-di-(3-sulfopropyl)-4,5,4',5'-dibenzothiacarbocyanine hydroxide Sensitizing dye III: Anhydro-5,5'-diphenyl-9 ethyl-3,3'-di-(3-sulfopropyl)oxacarbocyanine hydroxide Sensitizing dye IV: Anhydro-9-ethyl 3,3'-di-(3-sulfopropyl)-5,6,5'6'-dibenzoxacarbocyanine hydroxide Sensitizing dye V: Anhydro-3,3'-di-(3-sulfopropyl)-4,5-benzo-5'-methoxythiacyanine

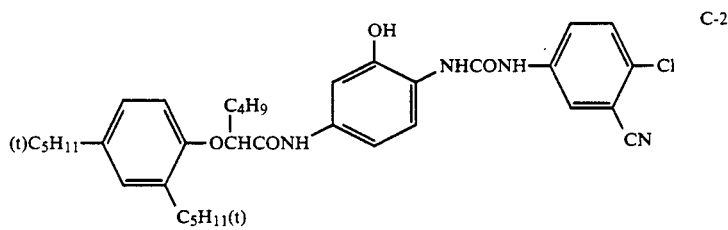

C-2

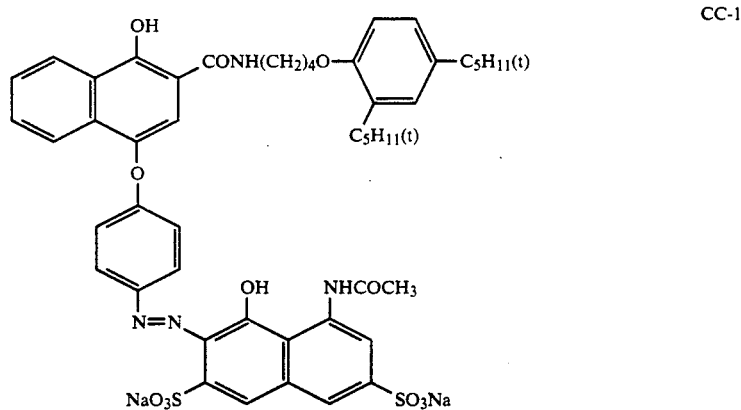

CC-1

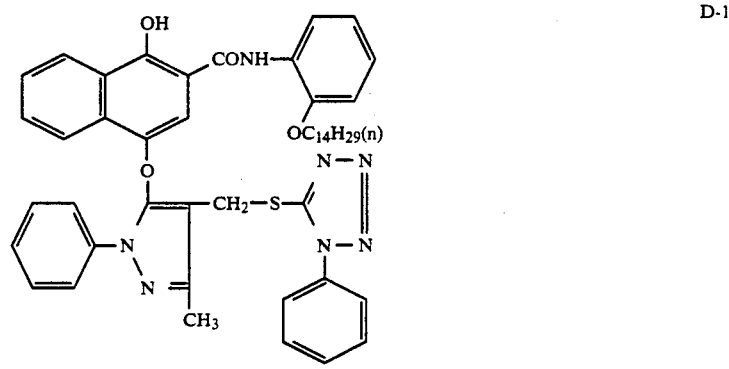

D-1

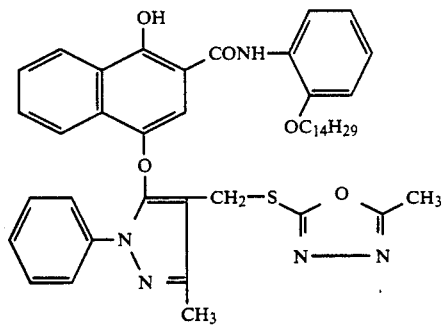
D-2
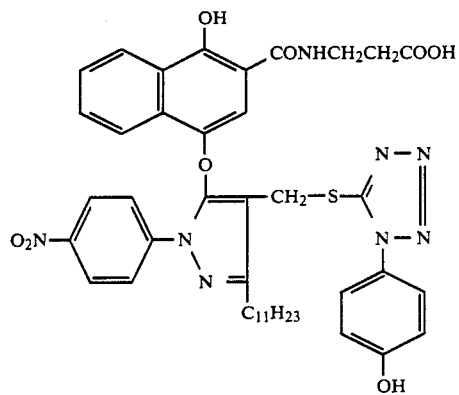
D-3
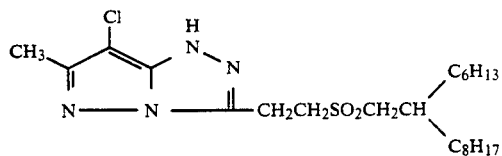
M-2
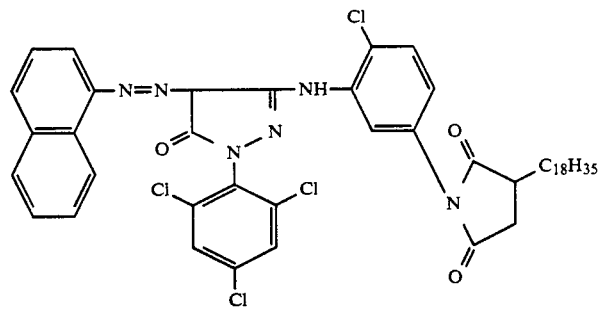
CM-1
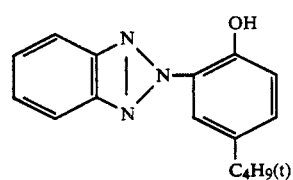
UV-3
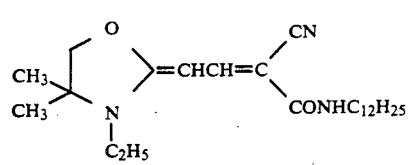
UV-4

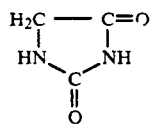

HS-1

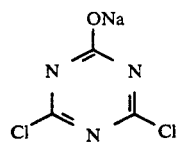

H-1

Further, Samples No. 25 through No. 33 were prepared in the same manner as in Sample No. 24 except that the comparative coupler Y-1 in the layers 9 and 10 of Sample No. 24 was changed as shown in Table 3.

These samples were exposed through an optical wedge in a usual manner, and processed in the following processing solutions in accordance with the following steps. The densities of the processed samples were measured through a blue filter. The results are shown in Table 3.

| Processing steps: | | |
|---|---|---|
| Color developing | (38° C.) | 3 minutes and 15 seconds |
| Bleaching | (38° C.) | 6 minutes and 30 seconds |
| Washing | (38° C.) | 3 minutes and 15 seconds |
| Fixing | (38° C.) | 6 minutes and 30 seconds |
| Washing | (38° C.) | 3 minutes and 15 seconds |
| Stabilizing | (38° C.) | 1 minute and 30 seconds |
| Drying | | |

The compositions of the processing solutions were as follows:

Color developer

| | |
|---|---|
| 4-Amino-3-methyl-N-ethyl-N-(β-hydroxyethyl)-aniline sulfate | 4.75 g |
| Anhydrous sodium sulfite | 4.25 g |
| Hydroxylamine ½ sulfate | 2.0 g |
| Anhydrous potassium carbonate | 37.5 g |
| Sodium bromide | 1.3 g |
| Trisodium nitrilotriacetate, monohydrate | 2.5 g |
| Potassium hydroxide | 1.0 g |
| Water was added to make total quantity 1 liter. | |
| Bleacher | |
| Ferric-ammonium ethylenediaminetetraacetate | 100.0 g |
| Diammonium ethylenediaminetetraacetate | 10.0 g |
| Ammonium bromide | 150.0 g |
| Glacial acetic acid | 10.0 ml |
| Water was added to make total quantity 1 liter. | |
| pH was adjusted to 6.0 with aqueous ammonia. | |
| Fixer | |
| Ammonium thiosulfate | 175.0 g |
| Anhydrous sodium sulfite | 8.5 g |
| Sodium metasulfite | 2.3 g |
| Water was added to make total quantity 1 liter. | |
| pH was adjusted to 6.0 with acetic acid. | |
| Stabilizer | |
| Formalin (37% solution) | 1.5 ml |
| Koniducks (product of KONICA Corporation) | 7.5 ml |
| Water was added to make total quantity 1 liter. | |

TABLE 3

| Sample No. | Coupler No. | ΔFog[*1] | Maximum density | Relative sensitivity |
|---|---|---|---|---|
| 24 (Comparative) | Y-1 | ±0 | 2.21 | 100 |
| 25 (Comparative) | Y-2 | +0.03 | 2.36 | 105 |

TABLE 3-continued

| Sample No. | Coupler No. | ΔFog[*1] | Maximum density | Relative sensitivity |
|---|---|---|---|---|
| 26 (Comparative) | Y-3 | +0.02 | 2.28 | 101 |
| 27 (Comparative) | Y-4 | +0.03 | 2.16 | 96 |
| 28 (Invention) | I-1 | +0.03 | 2.46 | 114 |
| 29 (Invention) | I-2 | +0.04 | 2.49 | 115 |
| 30 (Invention) | I-3 | +0.03 | 2.48 | 115 |
| 31 (Invention) | I-14 | +0.05 | 2.50 | 119 |
| 32 (Invention) | I-24 | +0.03 | 2.52 | 120 |
| 33 (Invention) | I-36 | +0.02 | 2.47 | 117 |

[*1]Difference in fog from Sample No. 24.
[*2]Relative value to the Sample No. 24's sensitivity which is set at 100.

As is apparent from Table 3, the yellow coupler of the invention improves the density and sensitivity without increasing fog.

EXAMPLE 4

Samples No. 34 through No. 39 were prepared by controlling the amounts of yellow couplers and tricresyl phosphate in Samples No. 24, 27 and 30 to 33 while keeping the ratio thereof constant so that the densities of the yellow dye images are all the same. The samples were exposed through a MTF measuring pattern to a white light, and then processed in the same manner as in Example 3. The processed Samples were measured for the MTF values in a spatial frequency of 20 cycle/mm with a blue light in order to evaluate sharpness. The results are given in Table 4.

TABLE 4

| Sample No. | Coupler No. | MTF value* |
|---|---|---|
| 34 (Comparative) | Y-1 | 100 |
| 35 (Comparative) | Y-4 | 92 |
| 36 (Invention) | I-3 | 117 |
| 37 (Invention) | I-14 | 120 |
| 38 (Invention) | I-24 | 122 |
| 39 (Invention) | I-36 | 118 |

*Relative value to the Sample No. 34's MTF value which is set at 100.

As is apparent from Table 4, the yellow couplers of the invention effectively improve the sharpness.

EXAMPLE 5

The samples were prepared in the same manner as in Example 1, except that the exemplified couplers used in Example 1 were replaced by those shown in Table 5. The results are given in Table 5.

TABLE 5

| Sample No. | Coupler No. | Condition after storage |
|---|---|---|
| 40 (Invention) | II-1 | No deposition |
| 41 (Invention) | II-2 | " |
| 42 (Invention) | II-6 | " |
| 43 (Invention) | II-12 | " |
| 44 (Invention) | II-16 | " |

TABLE 5-continued

| Sample No. | Coupler No. | Condition after storage |
|---|---|---|
| 45 (Invention) | II-20 | " |
| 46 (Invention) | II-27 | " |
| 47 (Invention) | II-30 | " |
| 48 (Comparative) | Y-1 | " |
| 49 (Comparative) | Y-2 | Slight deposition |
| 50 (Comparative) | Y-3 | Serious deposition |

As is obvious from Table 5, every one of the yellow couplers of the invention shows no deposition and has an excellent aging stability in an emulsion.

EXAMPLE 6

A multilayered color paper, Sample No. 51, was prepared by coating the layers each having the same compositions as in Example 2 over a paper support laminated with polyethylene on both sides thereof.

Samples No. 52 through No. 59 were further prepared in the same manner as in Sample 51, except that the coupler of Layer 1 was replaced by those shown in Table 6, respectively. The samples were exposed wedgewise to light in a usual manner and were then processed in the same processing steps and solutions as in Example 2.

The results are shown in Table 6.

TABLE 6

| Sample No. | Coupler No. | Developer A Yellow | Developer A Magenta | Developer A Cyan | Developer B Yellow | Developer B Magenta | Developer B Cyan |
|---|---|---|---|---|---|---|---|
| 51 (Inv) | II-1 | 2.43 | 2.63 | 2.60 | 2.36 | 2.54 | 2.36 |
| 52 (Inv) | II-3 | 2.48 | 2.60 | 2.57 | 2.40 | 2.52 | 2.37 |
| 53 (Inv) | II-6 | 2.44 | 2.62 | 2.56 | 2.31 | 2.55 | 2.35 |
| 54 (Inv) | II-16 | 2.46 | 2.61 | 2.59 | 2.38 | 2.51 | 2.38 |
| 55 (Inv) | II-18 | 2.47 | 2.63 | 2.61 | 2.40 | 2.53 | 2.37 |
| 56 (Inv) | II-27 | 2.42 | 2.63 | 2.59 | 2.36 | 2.54 | 2.36 |
| 57 (Comp) | Y-1 | 2.01 | 2.60 | 2.60 | 1.76 | 2.55 | 2.39 |
| 58 (Comp) | Y-2 | 2.34 | 2.61 | 2.62 | 2.20 | 2.51 | 2.35 |
| 59 (Comp) | Y-3 | 2.14 | 2.62 | 2.58 | 2.01 | 2.50 | 2.38 |

As is obvious from Table 6 above, the samples containing the yellow coupler of the invention show less drop of the maximum densities and better color balance than the samples containing the comparative couplers, even where developed in developer B without benzyl alcohol.

EXAMPLE 7

A multilayered color photographic materials. Sample No. 60, was prepared by coating each of the layers having the same compositions as in Example 3 in sequence on a triacetyl cellulose support.

Further, Samples No. 61 through No. 68 were prepared in the same manner as in Sample No. 60, except that comparative coupler Y-1 used in Layers 9 and 10 were replaced by those shown in Table 7.

The samples were exposed wedgewise to light in a usual manner and then processed in the same processing steps and solutions as in Example 3. The densities of the samples were measured with a blue filter. The results are shown in Table 7.

TABLE 7

| Sample No. | Coupler No. | ΔFog*1 | Maximum density | Relative sensitivity*2 |
|---|---|---|---|---|
| 60 | Y-1 (Comp) | ±0 | 2.24 | 100 |
| 61 | Y-2 (Comp) | +0.04 | 2.38 | 106 |
| 62 | Y-3 (Comp) | +0.02 | 2.31 | 104 |
| 63 | II-1 (Inv) | +0.04 | 2.49 | 115 |
| 64 | II-3 (Inv) | +0.03 | 2.48 | 118 |
| 65 | II-6 (Inv) | +0.04 | 2.46 | 112 |
| 66 | II-16 (Inv) | +0.02 | 2.48 | 120 |
| 67 | II-18 (Inv) | +0.04 | 2.50 | 117 |
| 68 | II-27 (Inv) | +0.02 | 2.47 | 118 |

*1Fog difference from that of Sample No. 60
*2Sensitivity relative to that of Sample No. 60, which is set at 100.

As is obvious from Table 7 above, the yellow coupler of the invention can improve both density and sensitivity without increasing fog.

EXAMPLE 8

Samples No. 69 to 74 were prepared by controlling the amounts of yellow coupler and tricresyl phosphate in Samples No. 61, 62, 64, 66, and 68, while keeping the ratio thereof constant, so that the densities of the yellow dye images are all the same. The samples were processed in the same manner as in Example 4. The processed samples were measured for the MTF values in a spatial frequency of 10 cycles/mm with a blue light in order to evaluate sharpness.

The results are given in Table 8.

TABLE 8

| Sample No. | Coupler No. | MTF value* |
|---|---|---|
| 69 (Comparative) | Y-1 | 100 |
| 70 (Comparative) | Y-2 | 103 |
| 71 (Invention) | II-3 | 116 |
| 72 (Invention) | II-16 | 118 |
| 73 (Invention) | II-18 | 115 |
| 74 (Invention) | II-27 | 115 |

*MTF value relative to that of Sample No. 69, which is set at 100

As is obvious from Table 8 above, the yellow coupler of the invention is effective to improve sharpness.

What is claimed is:

1. A silver halide light-sensitive color photographic material comprising a support and, provided thereon, photographic component layers including at least one silver halide light-sensitive layer containing at least one coupler represented by Formula I

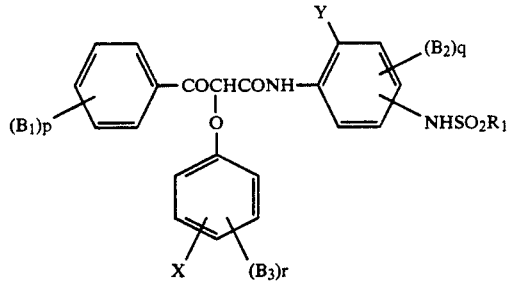

wherein $R_1$ represents a substituted or unsubstituted alkyl group; X represents an alkylsulfonyl group having 1 to 2 carbon atoms, a sulfamoyl group, an alkylsulfamoyl group having 1 to 5 carbon atoms, an alkylsulfonylamino group having 1 to 4 carbon atoms, a perfluoroalkylcarbonylamino group having 1 to 6 carbon atoms, a carbamoyl group, or an alkylcarbamoyl group having 1 to 3 carbon atoms, Y represents a halogen atom, an alkoxy group or an alkylamino group; $B_1$, $B_2$ and $B_3$ represent independently a substituent; and p, q and r represent independently integers of 0 to 3, wherein a distribution coefficient of a corresponding compound phenol in which said hydrophilic substituent represented by X is assumed to be introduced is not more than 1, and X and $B_3$ are joined independently at a m- or p-position to an oxygen atom bound to an active site of a coupler residue.

2. The photographic material of claim 1, wherein said distribution coefficient is not more than 0.

* * * * *